(12) United States Patent
Wang et al.

(10) Patent No.: US 9,610,325 B2
(45) Date of Patent: Apr. 4, 2017

(54) METHOD FOR INHIBITING EUPTX3 TO TREAT NASOPHARYNGEAL CARCINOMA BY AMINO ACID SEQUENCE

(71) Applicant: NATIONAL CHENG KUNG UNIVERSITY, Tainan (TW)

(72) Inventors: Ju-Ming Wang, Tainan (TW); Yu-Wei Hsiao, Chiayi (TW); Jhih-Ying Chi, New Taipei (TW); Shao-Ming Wang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 50 days.

(21) Appl. No.: 14/505,661

(22) Filed: Oct. 3, 2014

(65) Prior Publication Data

US 2015/0025018 A1 Jan. 22, 2015

Related U.S. Application Data

(63) Continuation-in-part of application No. 14/043,914, filed on Oct. 2, 213, now abandoned.

(30) Foreign Application Priority Data

Jun. 7, 2013 (TW) .............................. 102120429 A

(51) Int. Cl.
| | |
|---|---|
| *A61K 38/00* | (2006.01) |
| *A61P 35/00* | (2006.01) |
| *A61K 38/16* | (2006.01) |
| *C07K 1/00* | (2006.01) |
| *C07K 14/00* | (2006.01) |
| *C07K 17/00* | (2006.01) |
| *A61K 38/17* | (2006.01) |
| *C07K 14/71* | (2006.01) |

(52) U.S. Cl.
CPC .......... *A61K 38/1709* (2013.01); *A61K 38/00* (2013.01); *A61K 38/16* (2013.01); *C07K 14/71* (2013.01)

(58) Field of Classification Search
None
See application file for complete search history.

(56) References Cited

U.S. PATENT DOCUMENTS

| | | | |
|---|---|---|---|
| 8,003,109 B2 | 8/2011 | Bottazzi et al. | |
| 2005/0043230 A1 | 2/2005 | Presta et al. | |
| 2007/0071828 A1* | 3/2007 | Tseng ................... | A61K 35/48 424/528 |
| 2016/0347800 A1* | 12/2016 | Wang ................... | C07K 14/47 |

FOREIGN PATENT DOCUMENTS

WO 99/32516 A2 7/1999

OTHER PUBLICATIONS

Abcam, "Recombinant Human Pentraxin 3 (ab85335)", available online at http://www.abcam.com/recombinant-human-pentraxin-3-protein-ab85335.html, 3 pages (accessed on Apr. 11, 2016).*
EMBL Database, "Protein Expression and Purification Core Facility, Choice of Expression Systems," available online at https://www.embl.de/pepcore/pepcore_services/cloning/choice_expression_systems/, 7 pages (accessed on Dec. 13, 2016).*
Changzhou City Guoyu Environmental S&T Co. Ltd.; Carboxy Methyl Cellulose use in the pharmaceutical industry ; Available Online at http://guoyukeji.blog.com/2011/07/08/%e3%80%80carboxy-methyl-cellulose-use-in-the-pharmaceutical-industry/, 1 page, Jul. 8, 2011.
UniProt Accesion No. H0WWH7, 1 page (First Available Oct. 22, 2012).
UniProt Accesion No. F71850 2 pages (First Available Jul. 27, 2011).
UniProt Accesion No. H2QNM9 1 page (First Available Mar. 21, 2012).
NCBI Database, Genbank Accession No. P26022, 6 pages (Sequence Last Updated May 18, 2010).
NCBI Database, Genbank Accession No. CAA44778, 1 page, Oct. 10, 1993.

\* cited by examiner

*Primary Examiner* — Hasan Ahmed
*Assistant Examiner* — Thea D'Ambrosio
(74) *Attorney, Agent, or Firm* — CKC & Partners Co., Ltd.

(57) ABSTRACT

The invention relates to a method for inhibiting euPTX3 to treat nasopharyngeal carcinoma by an amino acid sequence, comprising administering an effective amount of the amino acid sequence to a subject in need. The amino acid sequence can be used to inhibit euPTX3 from promoting the migration and invasion of nasopharyngeal carcinoma cells, promoting angiogenesis and inhibiting macrophage phagocytosis to further treat nasopharyngeal carcinoma.

2 Claims, 16 Drawing Sheets

Figure 1:
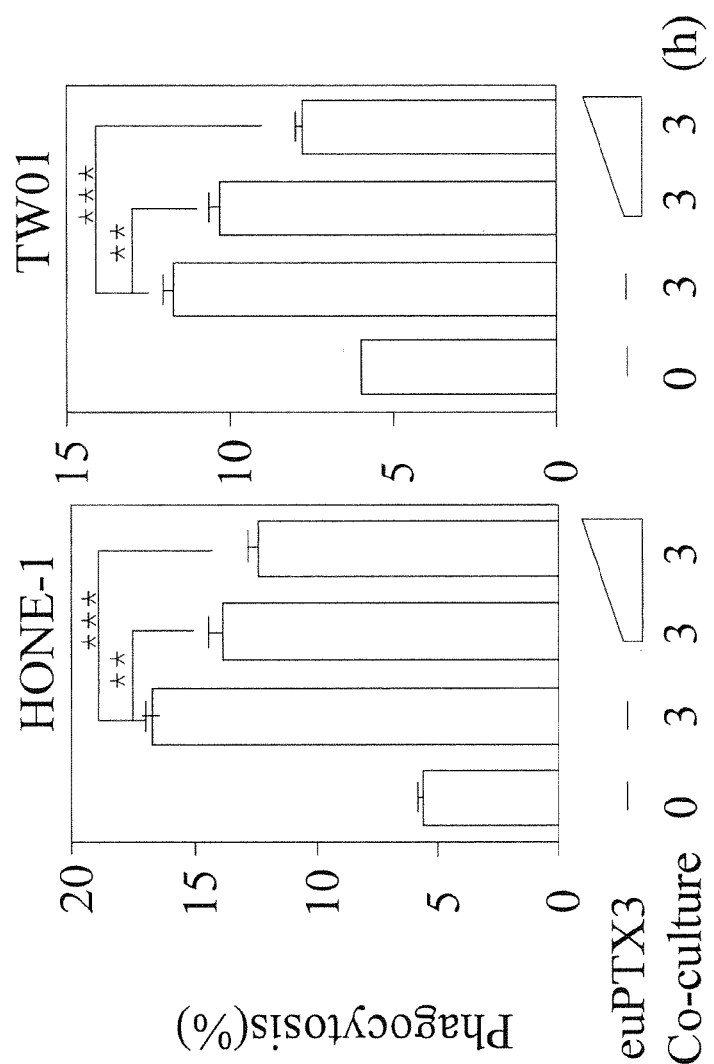

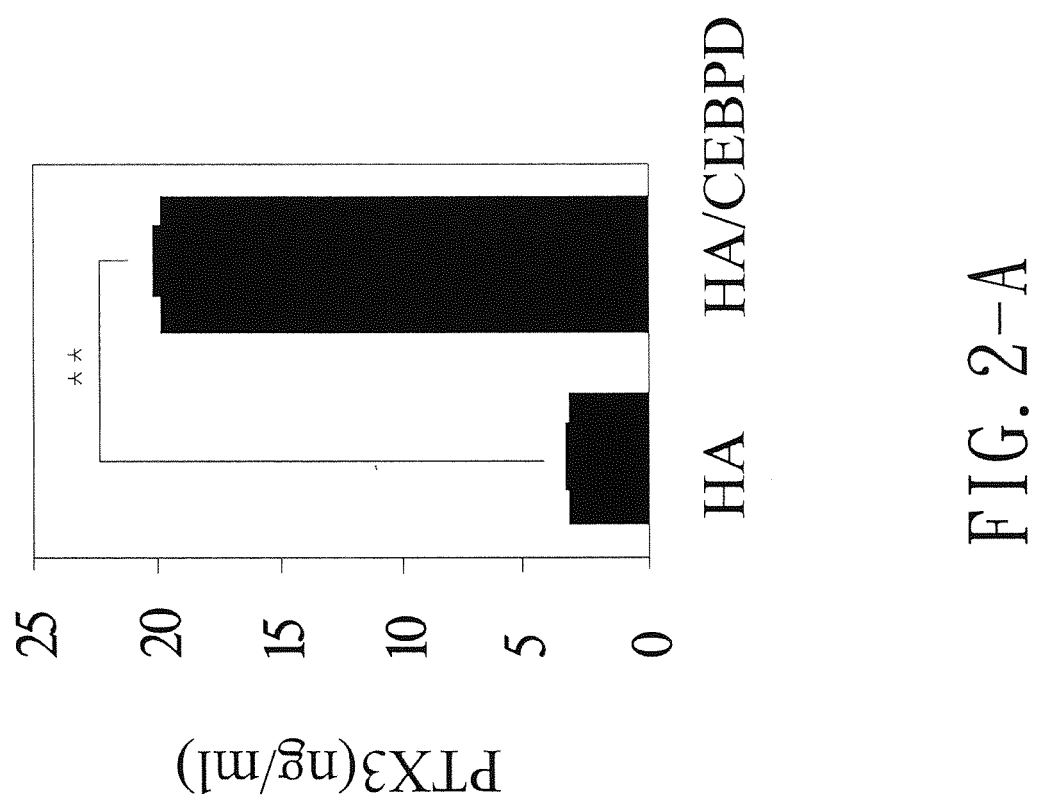
FIG. 2-A

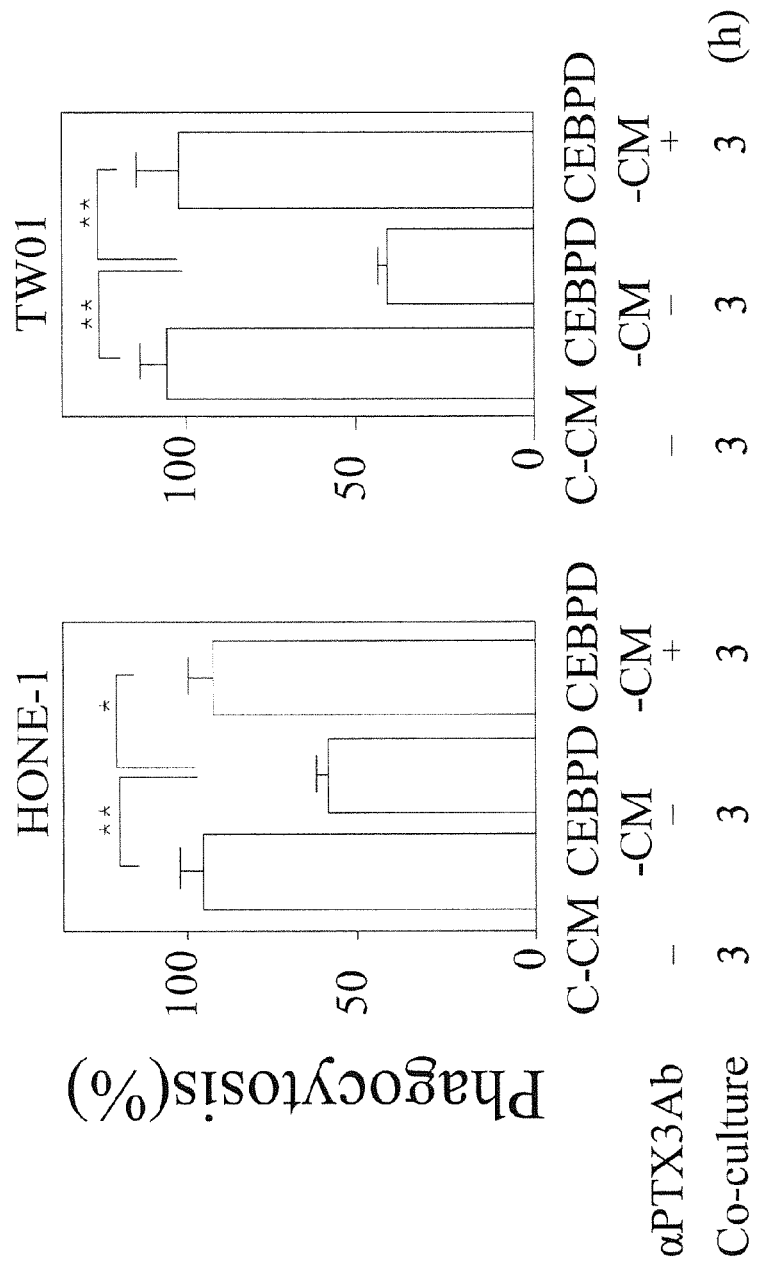
FIG. 2-B

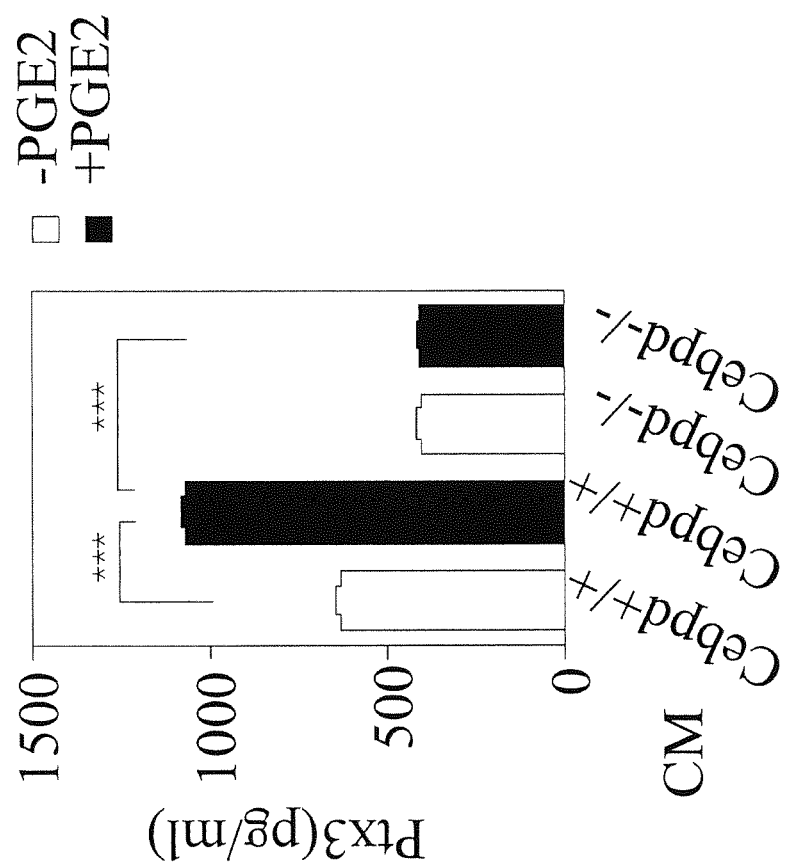
FIG. 2-C

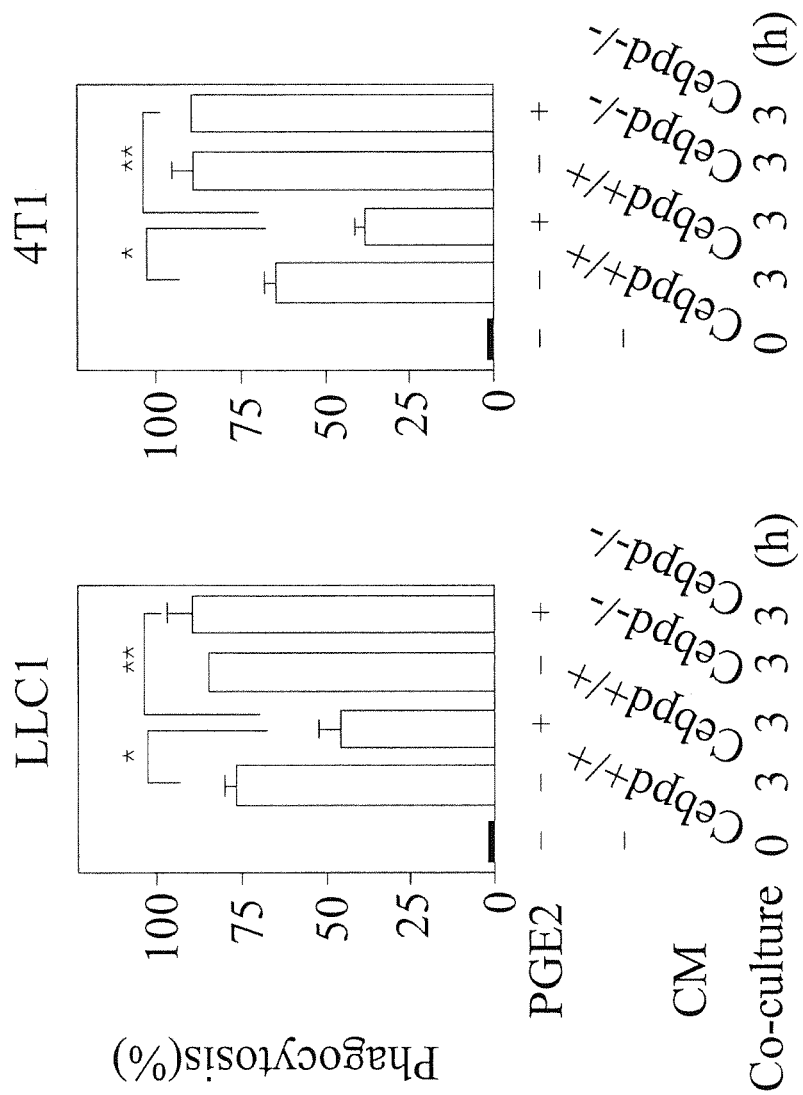
FIG. 2-D

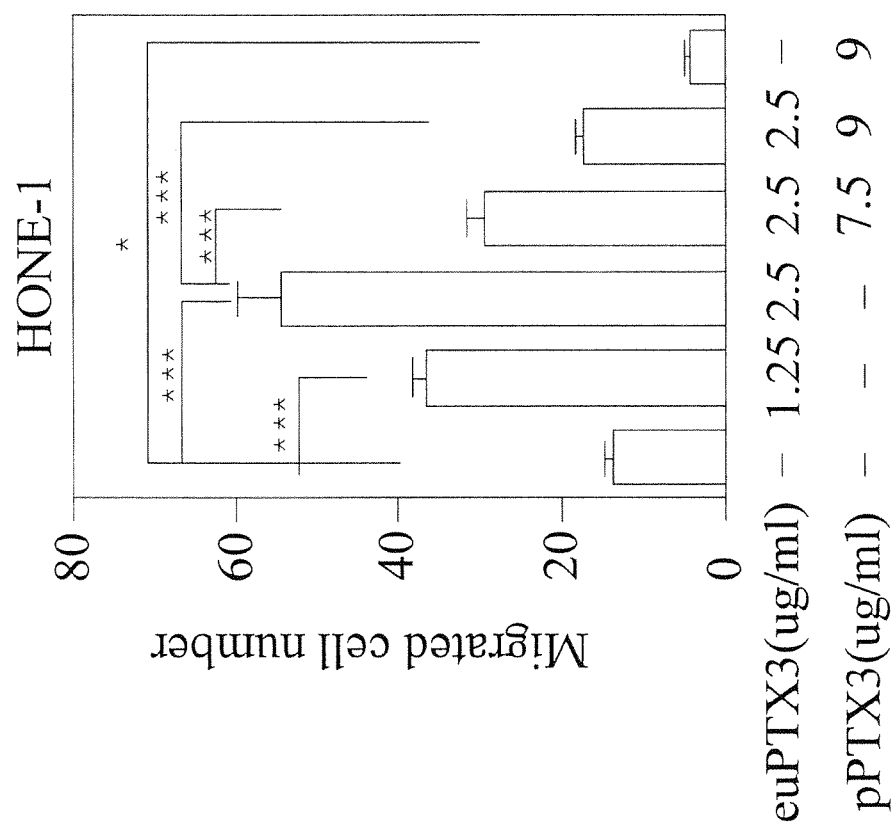
FIG. 3-A

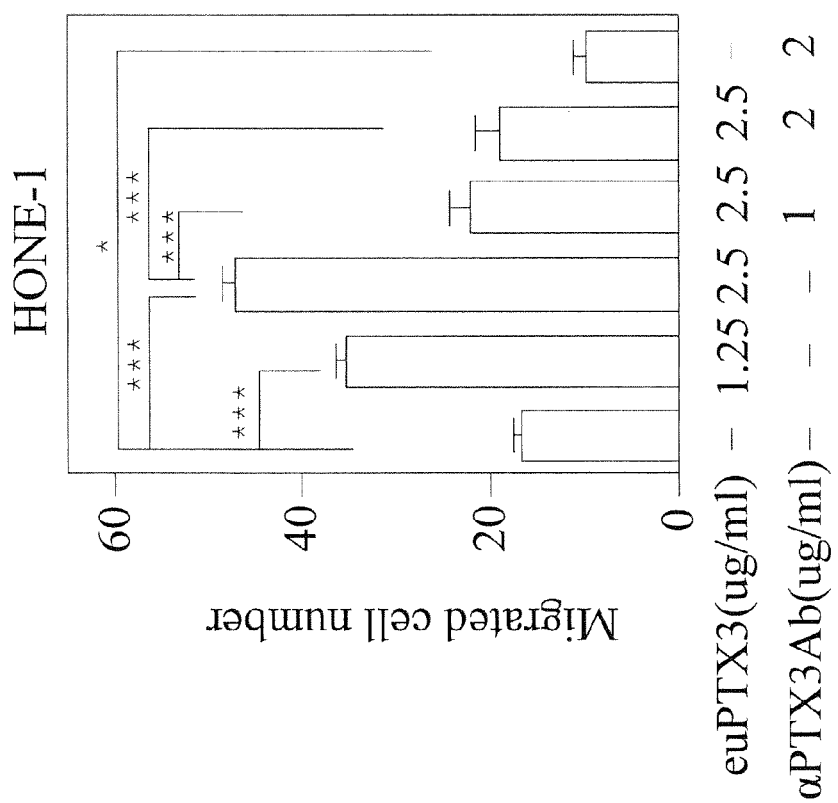
FIG. 3-B

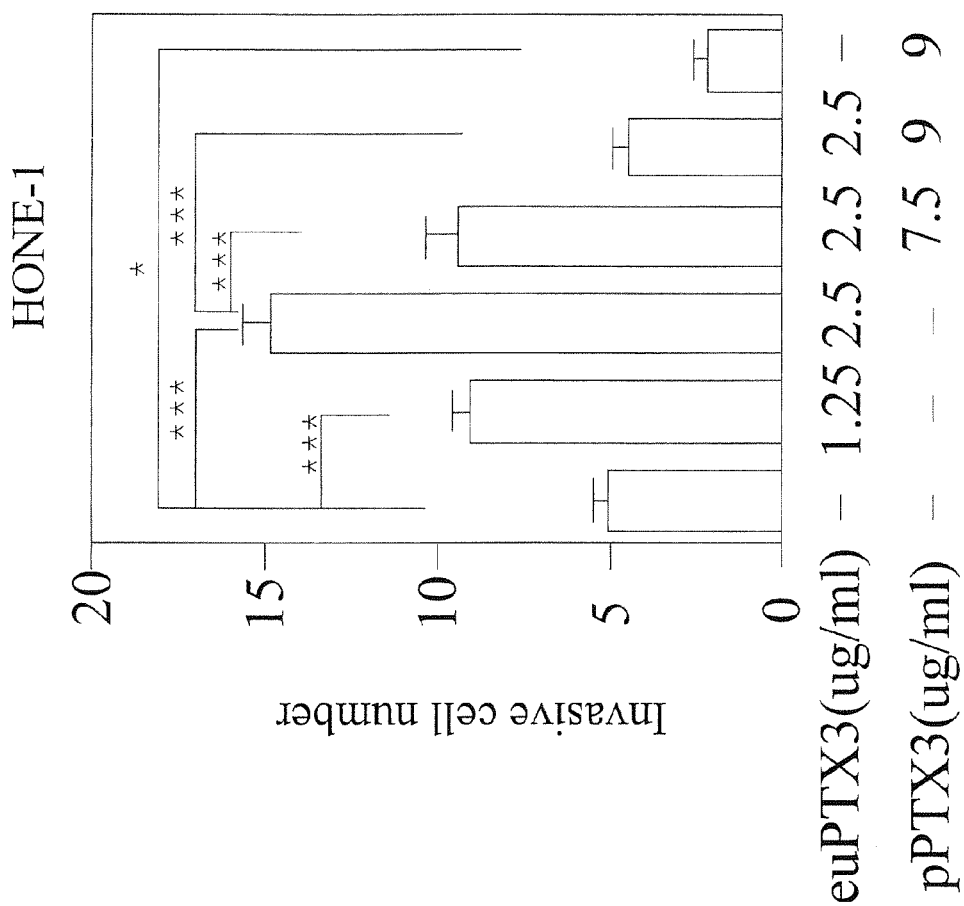
FIG. 3-C

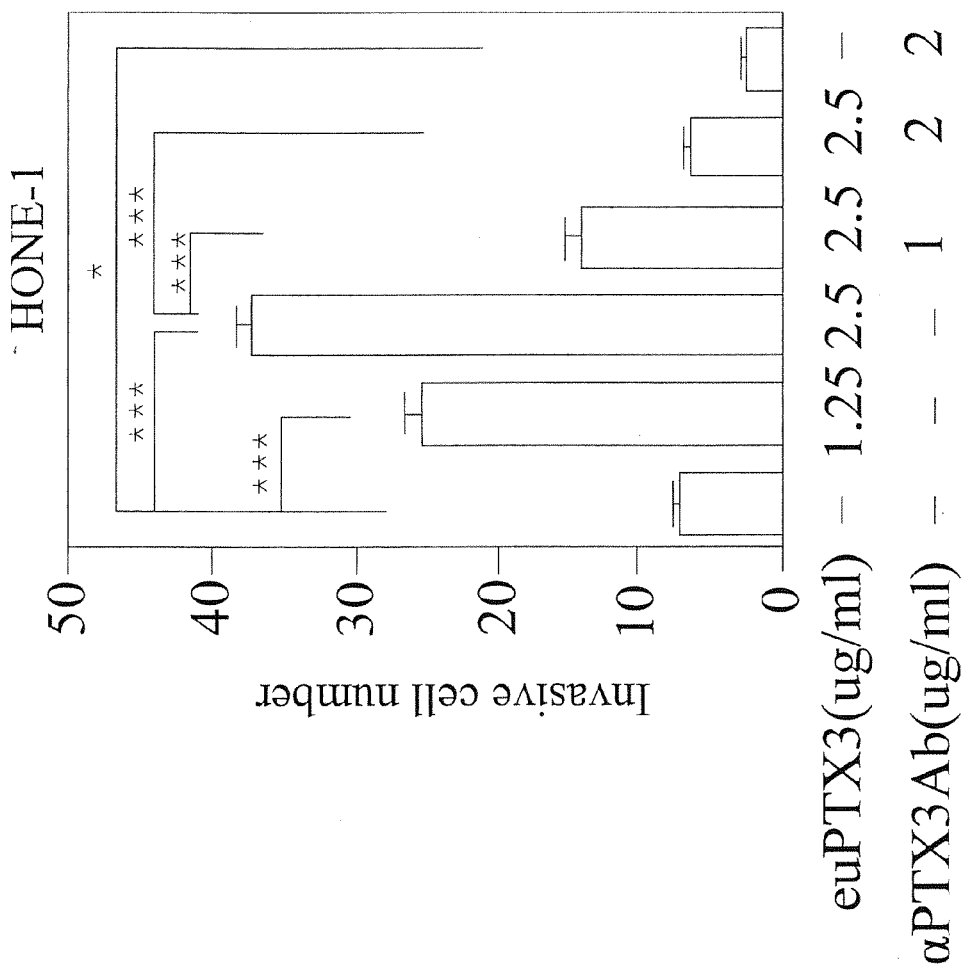
FIG. 3-D

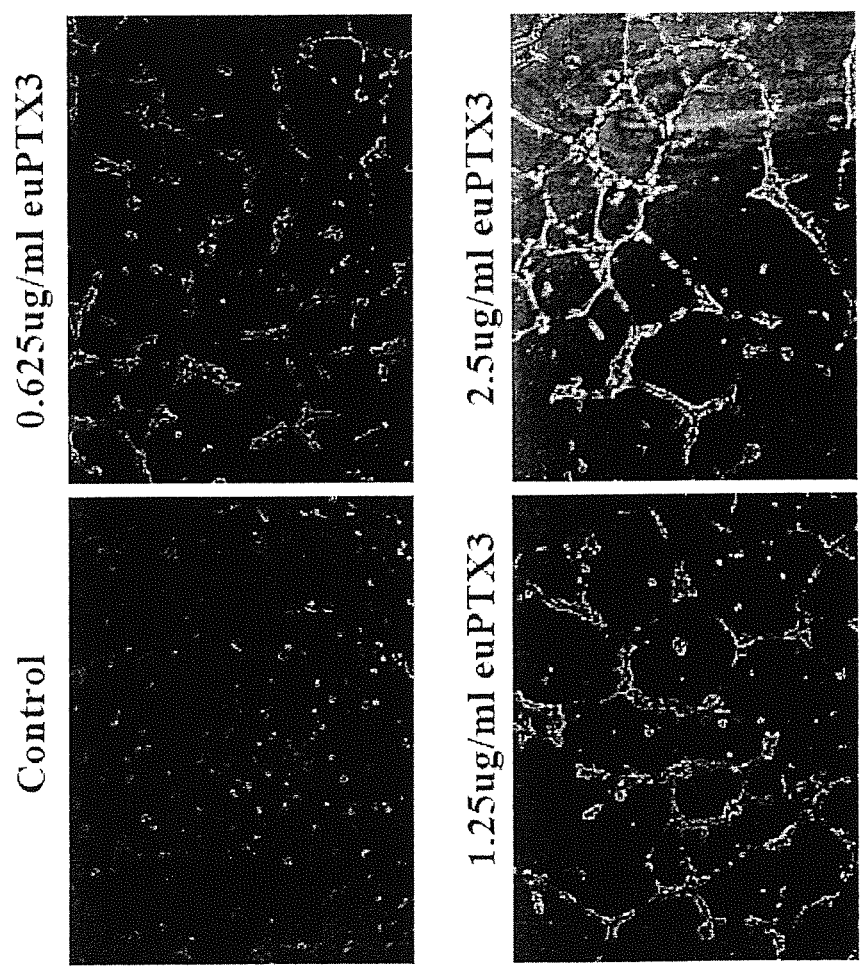
FIG. 4-A

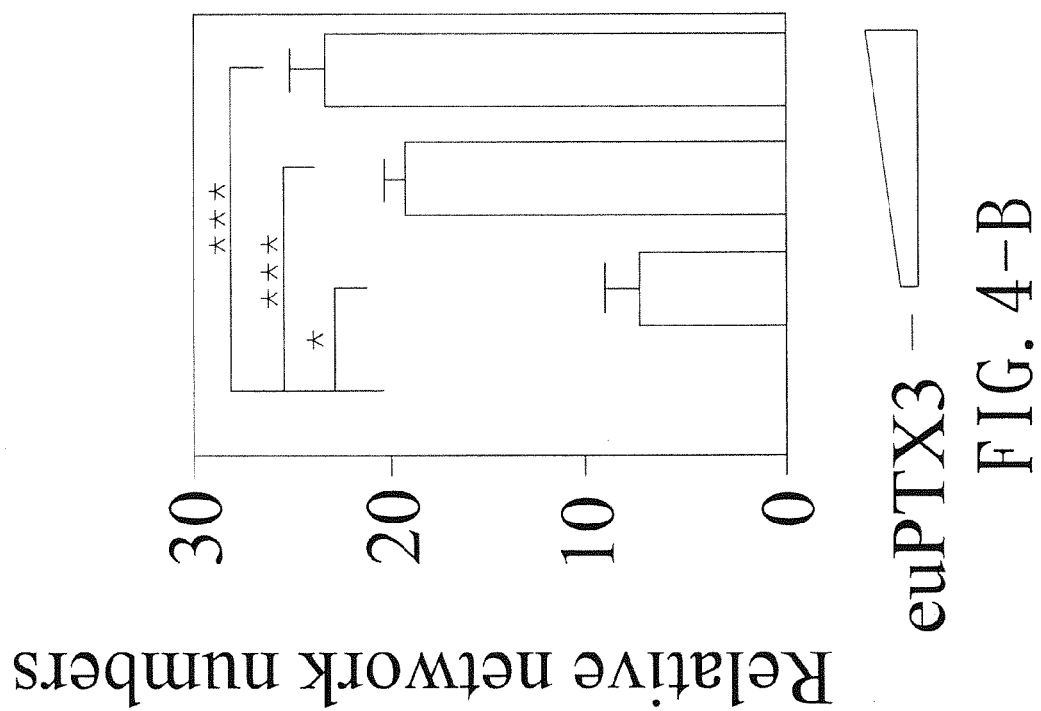
FIG. 4-B

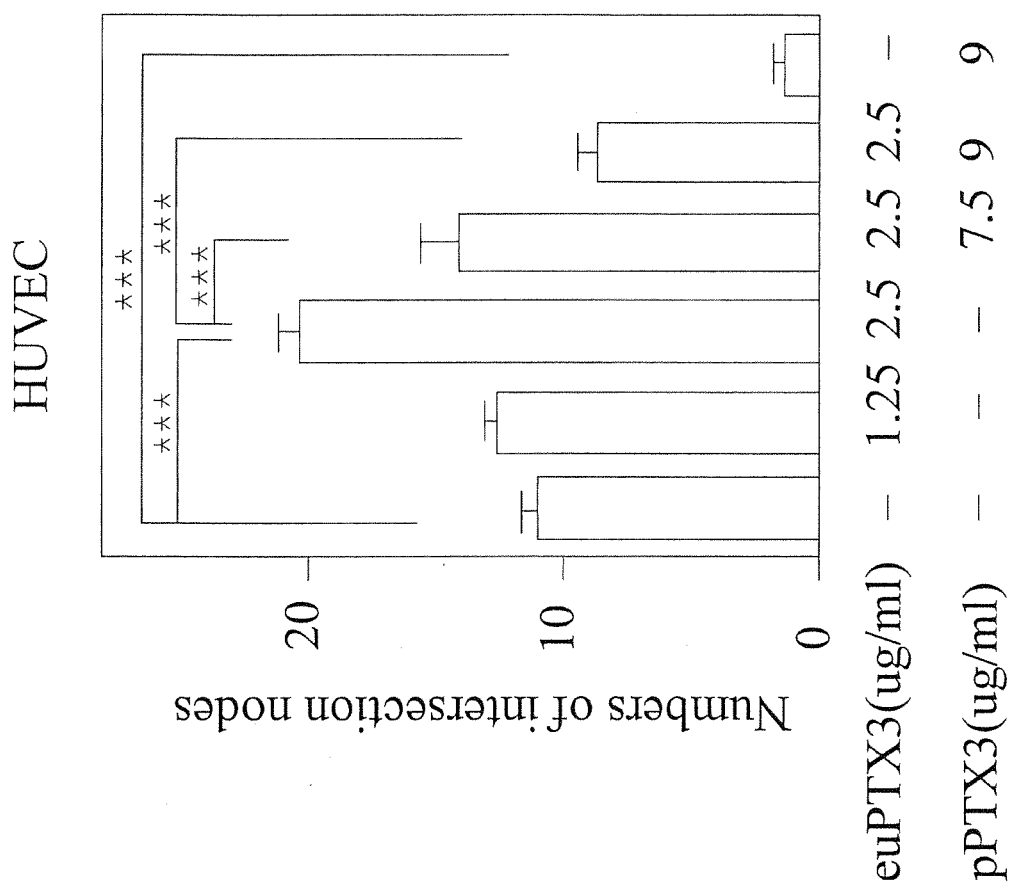
FIG. 5-A

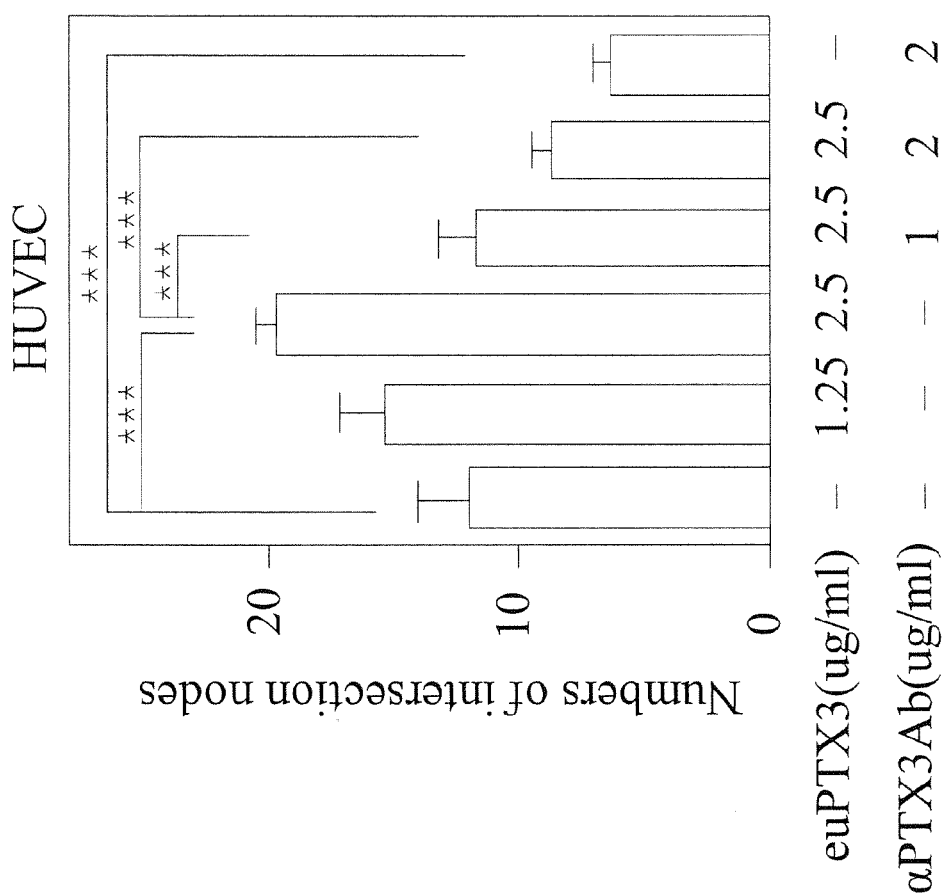
FIG. 5-B

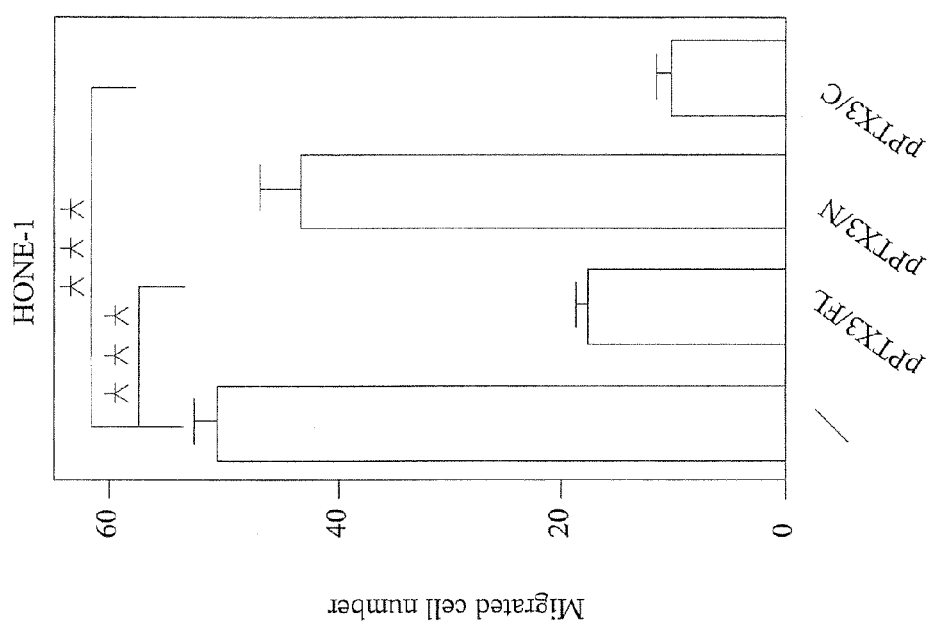
FIG. 6-A

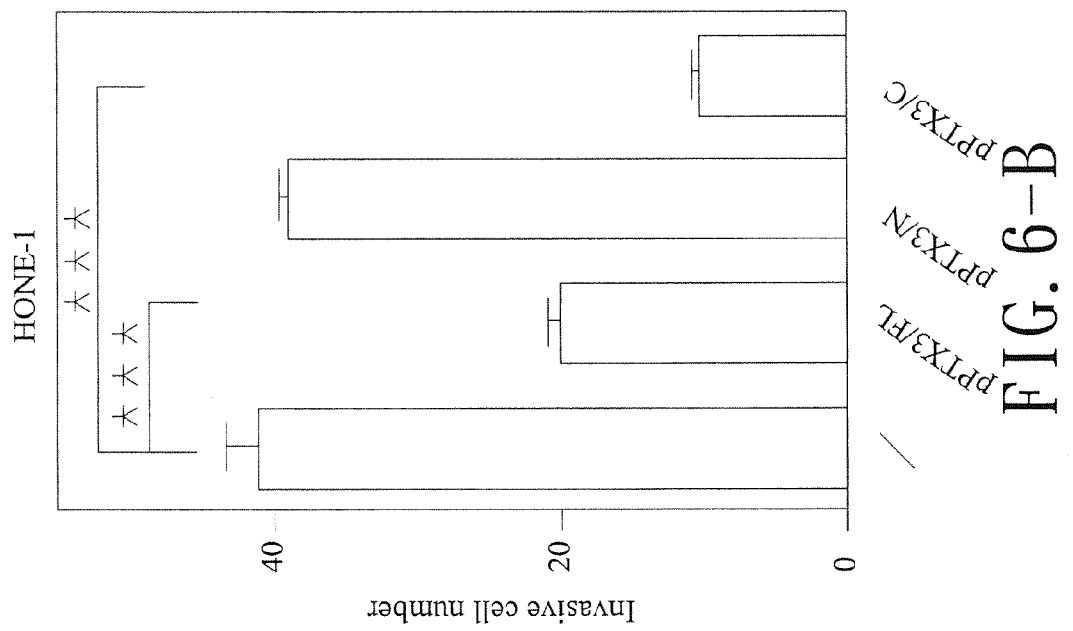
FIG. 6-B

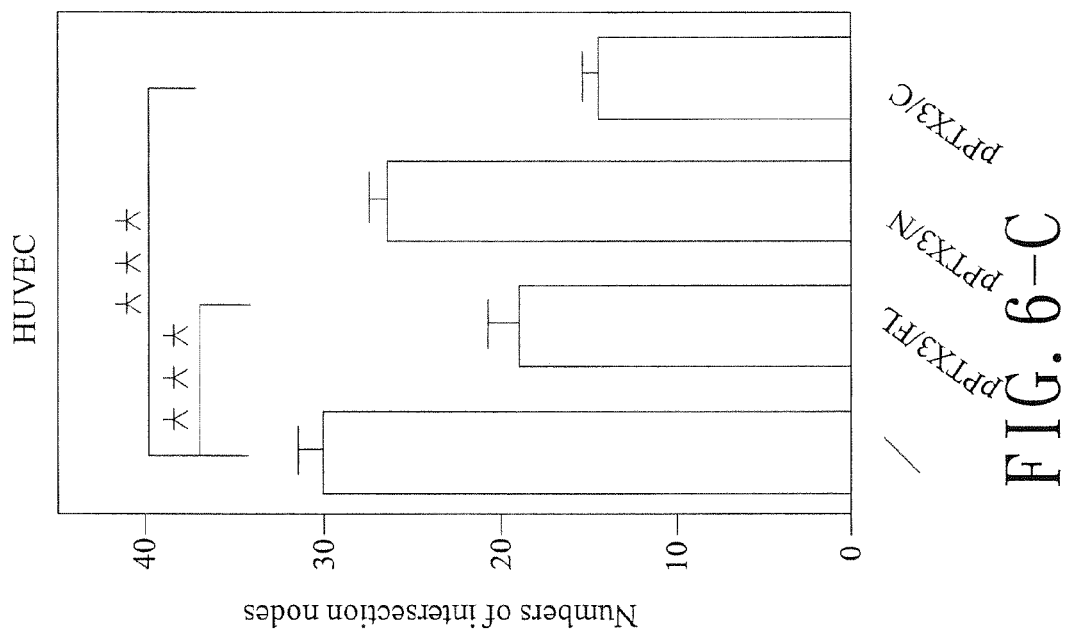
FIG. 6-C

SEQUENCE LISTING

<160> NUMBER OF SEQ ID NOS: 2

<210> SEQ ID NO 1
<211> LENGTH: 381
<212> TYPE: PRT
<213> ORGANISM: Homo sapiens

<400> SEQUENCE: 1

```
Met His Leu Leu Ala Ile Leu Phe Cys Ala Leu Trp Ser Ala Val Leu
1               5                   10                  15

Ala Glu Asn Ser Asp Asp Tyr Asp Leu Met Tyr Val Asn Leu Asp Asn
            20                  25                  30

Glu Ile Asp Asn Gly Leu His Pro Thr Glu Asp Pro Thr Pro Cys Ala
        35                  40                  45

Cys Gly Gln Glu His Ser Glu Trp Asp Lys Leu Phe Ile Met Leu Glu
    50                  55                  60

Asn Ser Gln Met Arg Glu Arg Met Leu Leu Gln Ala Thr Asp Asp Val
65                  70                  75                  80

Leu Arg Gly Glu Leu Gln Arg Leu Arg Glu Leu Gly Arg Leu Ala
            85                  90                  95

Glu Ser Leu Ala Arg Pro Cys Ala Pro Gly Ala Pro Ala Glu Ala Arg
            100                 105                 110

Leu Thr Ser Ala Leu Asp Glu Leu Leu Gln Ala Thr Arg Asp Ala Gly
        115                 120                 125

Arg Arg Leu Ala Arg Met Glu Gly Ala Glu Ala Gln Arg Pro Glu Glu
    130                 135                 140

Ala Gly Arg Ala Leu Ala Ala Val Leu Glu Glu Leu Arg Gln Thr Arg
145                 150                 155                 160

Ala Asp Leu His Ala Val Gln Gly Trp Ala Ala Arg Ser Trp Leu Pro
                165                 170                 175

Ala Gly Cys Glu Thr Ala Ile Leu Phe Pro Met Arg Ser Lys Lys Ile
            180                 185                 190

Phe Gly Ser Val His Pro Val Arg Pro Met Arg Leu Glu Ser Phe Ser
        195                 200                 205

Ala Cys Ile Trp Val Lys Ala Thr Asp Val Leu Asn Lys Thr Ile Leu
    210                 215                 220

Phe Ser Tyr Gly Thr Lys Arg Asn Pro Tyr Glu Ile Gln Leu Tyr Leu
225                 230                 235                 240

Ser Tyr Gln Ser Ile Val Phe Val Val Gly Gly Glu Asn Lys Leu
                245                 250                 255

Val Ala Glu Ala Met Val Ser Leu Gly Arg Trp Thr His Leu Cys Gly
            260                 265                 270

Thr Trp Asn Ser Glu Glu Gly Leu Thr Ser Leu Trp Val Asn Gly Glu
```

```
                    275                 280                 285
Leu Ala Ala Thr Thr Val Glu Met Ala Thr Gly His Ile Val Pro Glu
    290                 295                 300

Gly Gly Ile Leu Gln Ile Gly Gln Glu Lys Asn Gly Cys Cys Val Gly
305                 310                 315                 320

Gly Gly Phe Asp Glu Thr Leu Ala Phe Ser Gly Arg Leu Thr Gly Phe
                325                 330                 335

Asn Ile Trp Asp Ser Val Leu Ser Asn Glu Glu Ile Arg Glu Thr Gly
                340                 345                 350

Gly Ala Glu Ser Cys His Ile Arg Gly Asn Ile Val Gly Trp Gly Val
            355                 360                 365

Thr Glu Ile Gln Pro His Gly Gly Ala Gln Tyr Val Ser
    370                 375                 380

<210> SEQ ID NO 2
<211> LENGTH: 1146
<212> TYPE: DNA
<213> ORGANISM: Homo sapiens

<400> SEQUENCE: 2
atgcatctcc ttgcgattct gttttgtgct ctctggtctg cagtgttggc cgagaactcg      60
gatgattatg atctcatgta tgtgaatttg gacaacgaaa tagacaatgg actccatccc     120
actgaggacc ccacgccgtg cgcctgcggt caggagcact cggaatggga caagctcttc     180
atcatgctgg agaactcgca gatgagagag cgcatgctgc tgcaagccac ggacgacgtc     240
ctgcggggcg agctgcagag gctgcgggag gagctgggcc ggctcgcgga aagcctggcg     300
aggccgtgcg cgccggggc tcccgcagag gccaggctga ccagtgctct ggacgagctg     360
ctgcaggcga cccgcgacgc gggccgcagg ctggcgcgta tggagggcgc ggaggcgcag     420
cgcccagagg aggcggggcg cgccctggcc gcggtgctag aggagctgcg gcagacgcga     480
gccgacctgc acgcggtgca gggctgggct gcccggagct ggctgccggc aggttgtgaa     540
acagctattt tattcccaat gcgttccaag aagattttg gaagcgtgca tccagtgaga     600
ccaatgaggc ttgagtcttt tagtgcctgc atttgggtca aagccacaga tgtattaaac     660
aaaaccatcc tgttttccta tggcacaaag aggaatccat atgaaatcca gctgtatctc     720
agctaccaat ccatagtgtt tgtggtgggt ggagaggaga caaactggt tgctgaagcc     780 atggtttccc tgggaaggtg gacccacctg tgcggcacct ggaattcaga ggaagggctc     840
acatccttgt gggtaaatgg tgaactggcg gctaccactg ttgagatggc cacaggtcac     900
attgttcctg agggaggaat cctgcagatt ggccaagaaa agaatggctg ctgtgtgggt     960
ggtggctttg atgaaacatt agccttctct gggagactca caggcttcaa tatctgggat    1020
agtgttctta gcaatgaaga gataagagag accggaggag cagagtcttg tcacatccgg    1080
gggaatattg ttgggtgggg agtcacagag atccagccac atggaggagc tcagtatgtt    1140
tcataa                                                                1146
```

METHOD FOR INHIBITING EUPTX3 TO TREAT NASOPHARYNGEAL CARCINOMA BY AMINO ACID SEQUENCE

CROSS REFERENCE TO RELATED APPLICATION

This application is a continuation-in-part of application Ser. No. 14/043,914, filed on Oct. 2, 2013, which claims the benefits of the Taiwan Patent Application Ser. No. 102120429, filed on 7 Jun. 2013, the subject matter of which is incorporated herein by reference.

BACKGROUND OF THE INVENTION

1. Field of the Invention

The present invention relates to a method for inhibiting euPTX3 to treat nasopharyngeal carcinoma (NPC) by an amino acid sequence, more particularly for inhibition of euPTX3 from promoting the migration and invasion of nasopharyngeal carcinoma cells, promoting angiogenesis and inhibiting macrophage phagocytosis to further treat nasopharyngeal carcinoma.

2. Description of Related Art

Many researches reported that acute inflammation increases the probabilities of normal cells to become tumorigenic and enhances the occurring rate of cancer cell migration and invasion. Tumor-associated macrophages (TAM) are the most abundant immune cells within the tumor stroma and are required for a number of functions important for tumor progression, such as promoting tumor cell proliferation, angiogenesis, incessant matrix turnover and repressing the adaptive immune responses. Clinical investigations have shown that high levels of macrophage infiltration into tumors are associated with a poor prognosis.

PTX3 is a long pentraxin protein, whose mechanism of action is under study. In osteoblasts, prostaglandin E2 (PGE2) increases the translocation of transcription factor CCAAT/enhancer binding protein delta (CEBPD) from cytoplasm to nucleus by activating protein kinase A to result in an increased expression of insulin-like growth factor (IGF-1). A high expression level of CEBPD in inflammation indicates that CEBPD and its downstream target proteins play important roles in inflammation. In astrocytes, an increase of CEBPD is able to activate PTX3 protein to suppress the phagocytosis of damaged cells by macrophage, in relation to age-associated disorder, e.g. Alzheimer's disease. As such, most of prior arts disclosed the relation of CEBPD to PTX3 associated mechanisms. Nasopharyngeal carcinoma represents a unique tumor microenvironment where the epithelial tumor cells are surrounded by abundant infiltrating immune cells. During tumorigenesis, tumors can adapt to evade immunosurveillance by altering the properties and functions of the host's stromal and/or immune cells.

The invention connects PTX3 to tumor-associated macrophages and nasopharyngeal carcinoma. It suggests that PTX3 has abilities of promoting the migration of nasopharyngeal carcinoma cells and angiogenesis, and abilities of inhibiting macrophage phagocytosis, whereas PTX3 antibody and recombinant PTX3 protein of prokaryotes can inhibit the function as described above. Thus, an amino acid sequence for treating nasopharyngeal carcinoma has been developed in view of this novel finding and convenience of application.

A plurality of amino acid sequences available in nature shares at least 85% sequence homology with SEQ ID NO:1. For example, the amino acid sequence of pentraxin of *Otolemur garnettii* (uncharacterized protein, H0WWH7) has sequence homology of 86% with the Seq. ID No: 1 in the present invention. The amino acid sequence of pentraxin of *Callithrix jacchus* (F7I850) shares 92.1% sequence homology with the Seq. ID No: 1 in the present invention. H2QNM9 has disclosed a sequence having sequence homology of 98.1% with Seq. ID No: 1 in the present invention while P26022 has disclosed a sequence sharing 100% sequence homology with Seq. ID No: 1 in the present invention. However, the function of the amino acid sequences mentioned above is not revealed.

U.S. Pat. No. 8,003,109 (Bottazzi, et al.) has revealed a kind of pharmaceutical composition comprising a long pentraxin PTX3 that shares 95% sequence homology with Seq. ID No: 1 in the present invention. The long pentraxin PTX3 is used to treat infectious and inflammatory diseases, or tumor diseases as disclosed in the abstract. However, after reviewing the specification in details, it is clear that the anticancer activity reported above correlates closely with the leukocyte recruitment which occurs in the mouse as a result of recognition of the C1q by PTX3. In genetically modified mice, no such leukocyte recruitment occurs. Thus the anticancer activity of this pharmaceutical composition is based on leukocyte recruitment. The capability of leukocyte recruitment of the pharmaceutical composition presents that the pharmaceutical composition can also be applied to treat diseases caused by pathogens (such as bacteria, fungi, protozoa, or virus). The anticancer activity of the amino acid sequence revealed by Bottazzi and having 95% sequence homology with Seq. ID No: 1 is provided after binding to the ligand—C1q and the binding of the amino acid sequence to the C1q results in leukocyte recruitment. However, Bottazzi hasn't discussed the effect of this amino acid sequence on migration and invasion of nasopharyngeal carcinoma cells, angiogenesis and macrophage phagocytosis.

The present invention provides an amino acid sequence for inhibiting euPTX3 from promoting the migration and invasion of nasopharyngeal carcinoma cells, promoting angiogenesis and inhibiting macrophage phagocytosis so as to treat nasopharyngeal carcinoma effectively. The amino acid sequence is derived from PTX3 of prokaryotes (*E. coli*), and having at least 95% sequence homology with SEQ ID NO:1 while the amino acid sequence of SEQ ID NO:1 is preferred. Generally, the amino acid sequence whose sequence homology with SEQ ID NO:1 is larger than 95% has the same capability as SEQ ID NO:1 of inhibiting nasopharyngeal carcinoma cells.

SUMMARY OF THE INVENTION

In view of the above-mentioned problems, the object of the present invention is to provide an amino acid sequence which can be used to inhibit euPTX3 from promoting the migration and invasion of nasopharyngeal carcinoma cells, from promoting angiogenesis and from inhibiting macrophage phagocytosis to treat nasopharyngeal carcinoma.

An object of the present invention relates to a method for inhibiting euPTX3 to treat nasopharyngeal carcinoma, comprising administering an effective amount of an amino acid sequence to a subject in need, wherein the amino acid sequence comprises at least 95% sequence homology with SEQ ID NO:1 to inhibit euPTX3 from promoting the migration and invasion of nasopharyngeal carcinoma cells, promoting angiogenesis and inhibiting macrophage phagocytosis. According to an embodiment of the present invention, the amino acid sequence is SEQ ID NO:1.

Another object of the present invention relates to a method for inhibiting euPTX3 to treat nasopharyngeal carcinoma, comprising administering an effective amount of an amino acid sequence to a subject in need, wherein the amino acid sequence comprises at least 95% sequence homology with a C-terminal amino acid 180-381 of SEQ ID NO:1 to inhibit euPTX3 from promoting the migration and invasion of nasopharyngeal carcinoma cells, promoting angiogenesis and inhibiting macrophage phagocytosis. According to an embodiment of the present invention, the amino acid sequence is the C-terminal amino acid 180-381 of SEQ ID NO:1

Disclosed herein is also about an amino acid sequence for inhibiting PTX3 to treat nasopharyngeal carcinoma by decreasing the migration and invasion of nasopharyngeal carcinoma cells, inhibiting angiogenesis and promoting macrophage phagocytosis.

An amino acid sequence can be used to inhibit euPTX3 from promoting the migration and invasion of nasopharyngeal carcinoma cells, promoting angiogenesis and inhibiting macrophage phagocytosis. In the foregoing description, the amino acid sequence has at least 90% sequence homology, such as 95% homology or 100% homology, with SEQ ID NO:1.

A pharmaceutical composition used to manufacture drugs for treating nasopharyngeal carcinoma in mammals, such as human patient, is further provided, comprising therapeutically effective dosage of amino acid sequence as described above in treatment, and one or more acceptable carriers in medicine. The carrier is selected from the group consisting of excipient, diluent, thickener, filler, binder, disintegration agent, lubricant, sebum or non-sebum base agent, surfactant, suspending agent, gelling agent, auxiliary agent, preservative, antioxidant, stabilizing agent, colorant and flavoring. Moreover, the pharmaceutical composition can be administered to a human patient by means of oral administration, injection, daub, or patch.

According to an embodiment of the present invention, a nucleic acid sequence which can be translated into an amino acid sequence such as one including an amino acid sequence of SEQ ID NO:1 is further provided.

BRIEF DESCRIPTION OF THE DRAWINGS

FIG. 1 is a diagram showing the effect of euPTX3 purified from mammals on macrophage phagocytosis activity.

FIG. 2-A is a diagram showing that PTX3 is increased in the conditioned medium of CEBPD-expressing THP-1 cells.

FIG. 2-B is a diagram showing that PTX3 antibody inhibits CEBPD-suppressed phagocytosis of cancer cells by activated macrophages.

FIG. 2-C is a diagram showing that Ptx3 is attenuated in PGE2-treated mouse Cebpd−/− bone marrow cells.

FIG. 2-D is a diagram showing that the conditioned medium of Cebpd+/+ macrophages attenuates LLC1 or 4T1 cells phagocytosed by activated mouse macrophages.

FIG. 3-A is a diagram showing that recombinant pPTX3 can inhibit recombinant euPTX3-induced migration of cancer cells.

FIG. 3-B is a diagram showing that PTX3 antibody inhibits euPTX3-induced migration of cancer cells.

FIG. 3-C is a diagram showing that pPTX3 can inhibit euPTX3-induced invasion of cancer cells.

FIG. 3-D is a diagram showing that PTX3 antibody inhibits euPTX3-induced invasion of cancer cells.

FIG. 4-A is a diagram showing the effect of euPTX3 on angiogenesis.

FIG. 4-B is a diagram showing that euPTX3 promotes angiogenesis.

FIG. 5-A is a diagram showing that recombinant pPTX3 can inhibit recombinant euPTX3-induced tube formation of HUVEC cells.

FIG. 5-B PTX3 antibody inhibits euPTX3-induced tube formation of HUVEC.

FIG. 6-A is a diagram showing that the recombinant pPTX3 (PTX3(pFL)), but not C-terminal truncation of pPTX3 (PTX3(N)), can inhibit HONE-1 cell migration.

FIG. 6-B is a diagram showing that the recombinant pPTX3 (PTX3(pFL)), but not C-terminal truncation of pPTX3 (PTX3(N)), can inhibit HONE-1 cell invasion.

FIG. 6-C is a diagram showing that the recombinant pPTX3 (PTX3(pFL)), but not C-terminal truncation of pPTX3 (PTX3(N)), can reduce tube formation of HUVEC.

DETAILED DESCRIPTION OF THE PREFERRED EMBODIMENT

An object of the present invention relates to a method for inhibiting euPTX3 to treat nasopharyngeal carcinoma, comprising administering an effective amount of an amino acid sequence to a subject in need, wherein the amino acid sequence comprises at least 95% sequence homology with SEQ ID NO:1 to inhibit euPTX3 from promoting the migration and invasion of nasopharyngeal carcinoma cells, promoting angiogenesis and inhibiting macrophage phagocytosis. According to an embodiment of the present invention, the amino acid sequence is SEQ ID NO:1.

Another object of the present invention relates to a method for inhibiting euPTX3 to treat nasopharyngeal carcinoma, comprising administering an effective amount of an amino acid sequence to a subject in need, wherein the amino acid sequence comprises at least 95% sequence homology with a C-terminal amino acid 180-381 of SEQ ID NO:1 to inhibit euPTX3 from promoting the migration and invasion of nasopharyngeal carcinoma cells, promoting angiogenesis and inhibiting macrophage phagocytosis. According to an embodiment of the present invention, the amino acid sequence is the C-terminal amino acid 180-381 of SEQ ID NO:1

An amino acid sequence for inhibiting euPTX3 to treat nasopharyngeal carcinoma is also disclosed, which can be used to inhibit euPTX3 from promoting the migration and invasion of nasopharyngeal carcinoma cells, promoting angiogenesis and inhibiting macrophage phagocytosis. The amino acid sequence has at least 95% sequence homology, such as 95% homology or 100% homology, with SEQ ID NO:1.

A pharmaceutical composition for treating nasopharyngeal carcinoma in mammals, comprises therapeutically effective dosage of amino acid sequence and one or more acceptable carriers in medicine. The mammal is a human patient. Moreover, the carrier is selected from the group consisting of excipient, diluent, thickener, filler, binder, disintegration agent, lubricant, sebum or non-sebum base agent, surfactant, suspending agent, gelling agent, auxiliary agent, preservative, antioxidant, stabilizing agent, colorant and flavoring.

It is noted that the pharmaceutical composition is used to manufacture drugs for treating nasopharyngeal carcinoma. The foregoing pharmaceutical composition is administered to a human patient by means of oral administration, injection, daub or patch. In addition, a nucleic acid sequence can be translated into an amino acid sequence such as one including an amino acid sequence of SEQ ID NO:1.

Hereinafter, an exemplary embodiment of the present invention will be described in detail with reference to the accompanying drawings.

The human monocyte cell line, THP-1 cell, shares many properties with human monocyte-purified macrophages and is used as a model to study immune responses in vitro. Moreover, phorbol 12-myristate 13-acetate (PMA)-differentiated THP-1 macrophages and macrophage colony-stimulating factor (M-CSF)-treated mouse primary macrophages have been suggested to have tumor-associated macrophages (TAM) characteristics. The primary amino acid sequence of PTX3 is all highly conserved between mice and humans.

EXAMPLE 1

Cell Culture and Treatment

Different cell lines including THP-1, NPC-TW01 [TW01] and HONE-1 were cultured in RPMI-1640 medium (Hyclone) containing 10% fetal bovine serum (FBS), 100 μg/ml streptomycin, and 100 units/ml penicillin. A mouse lung cancer cell line LLC1 was maintained in DMEM medium supplemented with 10% FBS, 100 μg/ml streptomycin and 100 units/ml penicillin. Mouse bone marrow mononuclear cells were obtained from the femur and tibia of mice and grown in RPMI-1640 medium containing 10% FBS and 25 ng/mL M-CSF (R&D systems Inc.). For mouse macrophage differentiation, mouse bone marrow mononuclear cells were grown in medium containing M-CSF and allowed to adhere. The adherent bone marrow-purified macrophages were then re-seeded in RPMI-1640 medium with 10% FBS. In this study, the dosage of PGE2 (Sigma) applied in every treatment is 15 ng/ml.

EXAMPLE 2

Phagocytosis Assay of euPTX3 Purified from Mammals

HONE-1 or TW01, were stained with a PKH-26 red fluorescent cell linker kit (Sigma) according to the manufacturer's instructions. $5 \times 10^4$ PKH-26-stained NPC cells were then treated with 300 and 600 ng/ml euPTX3 (purified from eukaryotic mouse myeloma cells, R&D Systems Inc.) or conditioned medium. After removing the PTX3 protein or conditioned medium, the experimental cells were reseeded and co-cultured with PMA-treated PKH-67-stained THP-1 cells for 3 h (the human monocyte cell line, THP-1 cells, can differentiate to macrophages by treating with PMA) and fluorescence signals were analyzed by flow cytometry. Phagocytosis activity was expressed as the percentage of green$^+$/red$^+$ dual-fluorescent cells in the fluorescein isothiocyanate (FITC$^+$) single-fluorescent cell population. The results as shown in FIG. 1, euPTX3 attenuates NPC cells (HONE-1 and TW01) phagocytosed by activated macrophages. Furthermore, the level of attenuation is directly proportional to the increasing concentration of euPTX3.

EXAMPLE 3

Analyzing the Effect of PTX3/Ptx3 Purified from Mammals on Macrophage Phagocytosis Activity At first, the conditional media were harvested from $1 \times 10^6$ stable THP-1 cells (with pCDNA3/HA backbone vector) or $1 \times 10^6$ stable CEBPD-expressing THP-1 cells (with pCDNA3/HA-CEBPD vector). The secreted PTX3 in conditioned media of above experimental cells were detected by human PTX3 ELISA Kit (R&D systems Inc.). As shown in FIG. 2-A, PTX3 is increased in the conditioned medium of CEBPD-expressing THP-1 cells.

After neutralizing PTX3 in conditioned medium with 1 ug/ml control antibody or PTX3 antibody (ab90807, Abcam) for 4 hours, $5 \times 10^4$ HONE-1 or $5 \times 10^4$ TW01 cells were co-cultured with PMA-treated PKH-67-stained THP-1 cells in above neutralized conditioned media for 3 hours. Phagocytosis activity was analyzed and expressed as the percentage of green$^+$/red$^+$ dual-fluorescent cells in the FITC$^+$ single-fluorescent cell population. As shown in FIG. 2-B, PTX3 antibody inhibits CEBPD-suppressed macrophage phagocytosis of cancer cells by activated macrophages.

The bone marrow mononuclear cells were obtained from the femur and tibia of C57BL/6 mice. For mouse macrophage differentiation, bone marrow cells were grown in RPMI-1640 medium (Hyclone) with 10% FBS (Gibco) and 25 ng/ml M-CSF (R&D systems Inc.). The adherent bone marrow-purified macrophages were then re-seeded in RPMI-1640 medium with 10% FBS and treated with or without 15 ng/ml PGE2 (Sigma) for 6 hours. After replacement with fresh RPMI-1640 medium and extra 24-h growth, the conditioned medium was harvested for detecting the Ptx3 level by a Ptx3 ELISA kit (R&D systems Inc.). As shown in FIG. 2-C, the conditioned media harvested from Cebpd+/+ or Cebpd−/− macrophages with or without PGE2 treatment. The level of PTX3 increased via CEBPD after PGE2 treatment in the conditioned media harvested from Cebpd+/+ macrophages, whereas the level of PTX3 wasn't affected by PGE2 treatment in the conditioned media harvested from Cebpd−/− macrophages.

Finally, $5 \times 10^4$ LLC1 or $5 \times 10^4$ breast cancer cell line 4T1 cells (labeled by PKH-26) co-cultured with activated mouse macrophages (labeled by PKH-67) in conditioned media for 3 hours. Phagocytosis activity was analyzed and expressed as the percentage of green$^+$/red$^+$ dual-fluorescent cells in the FITC$^+$ single-fluorescent cell population. As shown in FIG. 2-D, the level of PTX3 increased via CEBPD after PGE2 treatment in the conditioned media harvested from Cebpd+/+ macrophages, which can attenuate LLC1 or 4T1 cells phagocytosed by activated mouse macrophages.

In summary, PTX3/Ptx3 purified from mammals contributes to the suppression of nasopharyngeal carcinoma cells phagocytosed by activated macrophages.

EXAMPLE 4

Analyzing the Effect of PTX3 on Nasopharyngeal Carcinoma Cells Migration and Invasion $3 \times 10^4$ HONE-1 cells were seeded in the upper layer of boyden chamber. The upper and bottom layer was separated by a polyethylene terephthalate membrane. After 3 hours culture, the regular culture medium was replaced by serum-free medium in the upper layer, and the euPTX3 or pPTX3 as indicated amount in FIG. 3-A were added with serum-free media in the bottom layer. For 24 hours incubation, the migrated cells in the bottom layer were detected by 4', 6-diamidino-2-phenylindole (DAPI, Invitrogen). Activity of cell migration (migrated cell number) was calculated as the percentage of the fluorescence relative to the controls. As shown in FIG. 3-A, increased euPTX3 resulted in the increase of HONE-1 migration, whereas increased pPTX3 inhibited euPTX3-induced migration of HONE-1. That is, recombinant pPTX3 can inhibit recombinant euPTX3-induced migration of nasopharyngeal carcinoma cells.

$3 \times 10^4$ HONE-1 cells were seeded in the upper layer of boyden chamber. The upper and bottom layer was separated by a polyethylene terephthalate membrane. After 3 hours culture, the regular culture medium was replaced by serum-free medium in the upper layer, and the euPTX3 with or without binding PTX3 antibody as indicated in FIG. 3-B were added with serum-free media in the bottom layer. For 24 hours incubation, the migrated cells in the bottom layer were detected by DAPI. Activity of cell migration (migrated cell number) was calculated as the percentage of the fluorescence relative to the controls. As shown in FIG. 3-B, PTX3 antibody inhibits euPTX3-induced migration of HONE-1.

$3 \times 10^4$ HONE-1 cells were seeded in the upper layer of boyden chamber. The upper and bottom layer was separated by a matrigel (BD Biosciences)-coated polyethylene terephthalate membrane. After 3 hours culture, the regular culture medium was replaced by serum-free medium in the upper layer and the euPTX3 or pPTX3 as indicated in FIG. 3-C were added with serum-free media in the bottom layer. For 24 hours incubation, the migrated cells in the bottom layer were detected by DAPI. Activity of cell invasion (invasive cell number) was calculated as the percentage of the fluorescence relative to the controls. As shown in FIG. 3-C, pPTX3 inhibits euPTX3-induced invasion of cancer cells.

$3 \times 10^4$ HONE-1 cells were seeded in the upper layer of boyden chamber. The upper and bottom layer was separated by a polyethylene terephthalate membrane. After 3 hours culture, the regular culture medium was replaced by serum-free medium in the upper layer, and the euPTX3 with or without binding PTX3 antibody as indicated in FIG. 3-D were added with serum-free media in the bottom layer. For 24 hours incubation, the migrated cells in the bottom layer were detected by DAPI. Activity of cell invasion was calculated as the percentage of the fluorescence relative to the controls. As shown in FIG. 3-D, PTX3 antibody inhibits euPTX3-induced invasion of cancer cells.

In summary, pPTX3 protein can inhibit euPTX3-induced migration and invasion of nasopharyngeal carcinoma cells.

EXAMPLE 5

Analyzing the Effect of euPTX3 on Angiogenesis $2 \times 10^4$ human umbilical vein endothelial Cells (HUVEC) grew in serum-free ECM medium (ScienCell) with indicated amounts (as indicated in FIG. 4-A) of euPTX3 on pre-coated matrigel plates. After 12 hours incubation, the experimental cells were fixed with 4% paraformaldehyde for observation of the tube-formation morphology. Tube-like structures were quantified by counting the number of intersections between branches of endothelial cell networks (relative network numbers) in the whole field. Each condition in this experiment was repeated at least three times. The results as shown in FIG. 4-A and FIG. 4-B, euPTX3 promotes angiogenesis.

EXAMPLE 6

Analyzing the Effect of PTX3 on Angiogenesis $2 \times 10^4$ HUVEC grew in serum-free ECM medium with indicated amounts (as indicated in FIG. 5-A) of euPTX3 or pPTX3 on pre-coated matrigel plates. After 12 hours incubation, HUVEC were fixed with 4% paraformaldehyde for observation of the tube-formation morphology. Tube-like structures were quantified by counting the number of intersections between branches of endothelial cell networks (number of intersection nodes) in the whole field. As shown in FIG. 5-A, recombinant pPTX3 can inhibit recombinant euPTX3-induced tube formation of HUVEC cells.

$2 \times 10^4$ HUVEC grew in serum-free ECM medium with indicated amounts of euPTX3 on pre-coated matrigel plates. The euPTX3 with or without binding PTX3 antibody as indicated in FIG. 5-B were added with serum-free media. After 12 hours incubation, HUVEC were fixed with 4% paraformaldehyde for observation of the tube-formation morphology. Tube-like structures were quantified by counting the number of intersections between branches of endothelial cell networks in the whole field. As shown in FIG. 5-B, PTX3 antibody inhibits euPTX3-induced tube formation of HUVEC.

EXAMPLE 7

Identifying Functional Domain of pPTX3 involved in Migration, Invasion and Angiogenesis Above results infer that pPTX3 plays an opposite role from euPTX3, however the detailed mechanism remains elusive (perhaps involved in competitive binding or glycation). The results also show that euPTX3 promotes migration and invasion of nasopharyngeal carcinoma cells, promotes angiogenesis, and inhibits macrophage phagocytosis, whereas pPTX3 can inhibit euPTX3-induced effects as described above.

Continued from the preceding experiments, functional domain of pPTX3 involved in migration, invasion and angiogenesis was further identified. $3 \times 10^4$ HONE-1 cells were seeded in the upper layer of boyden chamber. The upper and bottom layer was separated by a polyethylene terephthalate membrane. After 3 hours culture, the regular culture medium was replaced by serum-free medium in the upper layer, and the recombinant pPTX3 (amino acids 18-381, pPTX3/FL, 225 nM, purified from *E. coli*, Abcam), N-terminal truncation of pPTX3 (amino acids 19-182, pPTX3/N, 225 nM, purified from *E. coli*) or C-terminal truncation of pPTX3 (amino acids 180-381, pPTX3/C, 225 nM, purified from *E. coli*) as indicated in FIG. 6-A were added with serum-free media in the bottom layer. For 24 hours incubation, the migrated cells in the bottom layer were detected by DAPI. Activity of cell migration (migrated cell number) was calculated as the percentage of the fluorescence relative to the controls. As shown in FIG. 6-A, pPTX3/FL and pPTX3/C, but not pPTX3/N, can significantly inhibit HONE-1 cell migration.

$3 \times 10^4$ HONE-1 cells were seeded in the upper layer of boyden chamber. The upper and bottom layer was separated by a polyethylene terephthalate membrane. After 3 hours culture, the regular culture medium was replaced by serum-free medium in the upper layer, and pPTX3/FL, pPTX3/N, or pPTX3/C as indicated in o FIG. 6-B were added with serum-free media in the bottom layer. For 24 hours incubation, the migrated cells in the bottom layer were detected by DAPI. Activity of cell invasion was calculated as the percentage of the fluorescence relative to the controls. As shown in FIG. 6-B, pPTX3/FL and pPTX3/C, but not pPTX3/N, can significantly inhibit HONE-1 cell invasion.

$2 \times 10^4$ HUVEC grew in serum-free ECM medium with indicated amounts (as indicated in FIG. 6-C) of pPTX3/FL, pPTX3/N, or pPTX3/C on pre-coated matrigel plates. After 12 hours incubation, HUVEC were fixed with 4% paraformaldehyde for observation of the tube-formation morphology. Tube-like structures were quantified by counting the number of intersections between branches of endothelial cell networks (number of intersection nodes) in the whole field. As shown in FIG. 6-C, pPTX3/FL and pPTX3/C, but not pPTX3/N, can significantly reduce tube formation of HUVEC.

In summary, as an exemplary embodiment, pPTX3 disclosed herein is SEQ ID NO:1 as claim, which can inhibit the migration and invasion of HONE-1 cells (NPC cell lines) and reduce tube formation of HUVEC, and thus can be a therapeutic target for treatment of nasopharyngeal carcinoma. Moreover, the nucleic acid sequence and the amino acid sequence of SEQ ID NO:1 are shown in sequence list.

According to the above description, in comparison with the traditional technique, an amino acid sequence for inhibiting PTX3 to treat nasopharyngeal carcinoma according to the present invention has the advantages as following:

1. The amino acid sequence can inhibit PTX3 from promoting the migration and invasion of nasopharyngeal carcinoma cells, promoting angiogenesis, and inhibiting macrophage phagocytosis to further treat nasopharyngeal carcinoma.
2. The amino acid sequence for inhibiting PTX3 can be further used in industry and manufactured by the methods of overexpression and purification of the recombinant protein.

What is claimed is:

1. A method for inhibiting eukaryotic long pentraxin protein ("euPTX3") to treat nasopharyngeal carcinoma, comprising administering an effective amount of an amino acid sequence expressed by a prokaryotic system to a subject in need thereof, wherein the amino acid sequence comprises the amino acid residues 180-381 of SEQ ID NO: 1, and wherein the amino acid sequence inhibits the migration and invasion of nasopharyngeal carcinoma cells, inhibits angiogenesis, and promotes macrophage phagocytosis.

2. The method of claim 1, wherein the prokaryotic system is E. coli.